United States Patent [19]

Costerton

[11] Patent Number: 4,542,169

[45] Date of Patent: Sep. 17, 1985

[54] BIOMEDICAL DEVICES CONTAINING ISOTHIAZOLONES TO CONTROL BACTERIA GROWTH

[75] Inventor: J. W. Costerton, Calgary, Canada

[73] Assignee: Rohm and Haas Company, Philadelphia, Pa.

[21] Appl. No.: 560,692

[22] Filed: Dec. 12, 1983

[51] Int. Cl.$^4$ ............................................. A61M 25/00
[52] U.S. Cl. ...................................... 523/121; 424/78; 424/83; 521/122; 604/265
[58] Field of Search ................. 521/121, 122; 604/265; 424/78, 83

[56] References Cited

U.S. PATENT DOCUMENTS

| | | | |
|---|---|---|---|
| 3,297,699 | 1/1967 | Schmidt et al. | 604/265 |
| 3,598,127 | 8/1971 | Wepsic | 604/265 |
| 3,755,224 | 8/1973 | Lutz, Jr. . | |
| 3,801,575 | 4/1974 | Lewis et al. | 523/122 |
| 3,896,813 | 7/1975 | Kurtz . | |
| 4,086,297 | 4/1978 | Rei et al. . | |
| 4,105,431 | 8/1978 | Lewis et al. . | |
| 4,243,403 | 1/1981 | Lewis et al. | 523/122 |
| 4,381,380 | 4/1983 | LeVeen et al. . | |

OTHER PUBLICATIONS

J. Biomed. Materials Res.; 13, 623–630, (1979).
Greco, et al., Ann. Surg. 195, (No. 2), 168, (1982).

*Primary Examiner*—Lester L. Lee
*Attorney, Agent, or Firm*—Terence P. Strobaugh

[57] ABSTRACT

The control of bacterial growth in biomedical devices using isothiazolones.

16 Claims, No Drawings

BIOMEDICAL DEVICES CONTAINING ISOTHIAZOLONES TO CONTROL BACTERIA GROWTH

BACKGROUND OF THE INVENTION

1. Field of the Invention

This invention relates to biomedical devices possessing microbiocidal or antimicrobial properties. It also relates to control of sessile bacterial growth, especially that growth at the point of contiguity between device and body tissues.

2. Description of Related Art

U.S. Pat. No. 3,755,224 discloses vinyl chloride compositions possessing biocidal properties and articles thereof wherein the compositions are produced from a vinyl chloride resin containing a 3-isothiazolone and a liquid plasticizer.

U.S. Pat. No. 4,086,297 discloses solid thermoplastic resin compositions containing from 1 to 80% of a microbiocide wherein the microbiocide and a first thermoplastic resin composition are blended and further mixed with a second thermoplastic resin to provide resistance against microbiocidal attack on the second thermoplastic resin composition. Neither of these patents disclose the use of such materials for biomedical devices.

U.S. Pat. No. 4,105,431 discloses the maximum dilution of 3-isothiazolone which will control several organisms. However, the patent does not disclose the treatment of living hosts.

U.S. Pat. No. 3,896,813 discloses natural or synthetic suture material impregnated with an antibiotic to protect the suture material from biological contamination during storage.

Van Noort et al., *J. Biomed. Materials Res.* 13, 623–630 (1979), discloses silicone rubbers useful for hydrocephalus shunts impregnated with gentamicin sulfate.

Greco et al., *Ann. Surg.*, 195 (No. 2), 168 (1982), discloses polytetrafluoroethylene grafts bonded to oxacillin (a negatively charged antibiotic) using a cationic surfactant-benzalkonium chloride. The bonded grafts are useful to combat local contamination with Staph. aureus when placed in the infrarenal aorta of dogs.

The last three references all use naturally occurring antibiotics which give rise to resistant strains of bacteria.

See also U.S. Pat. No. 4,381,380 and references cited therein. U.S. Pat. No. 4,381,380 describes urethane cathethers made biocidal by soaking in iodine solutions. The drawbacks are that iodine is irritating, particularly, to mucosal surfaces. Iodine cannot be incorporated uniformly into a polymer because of volatility. The use of iodine is limited to urethanes which complex the iodine. Isothiazolones, however, can be used with a wide variety of useful elastomers, particularly rubber, silicone and plasticized vinyl.

"Antibiotic" means a chemical substance produced by microorganisms which has the capacity, in dilute solutions, to inhibit the growth of or to destroy bacteria and other microorganisms and is intended to embrace both naturally-produced (by microorganisms) and synthetic chemicals. Although antibiotics control a wide variety of living pathogenic organisms which occur in living mammalian hosts, many hosts demonstrate allergic responses when treated with antibiotics. Microorganisms tend to develop resistant mutants or strains upon exposure to naturally derived antibiotics. Further, antibiotics are difficult and costly to produce on a large scale. Also, heat causes antibiotics to lose their activity.

I have observed that the increasing use of a variety of medical prostheses made of a variety of materials including, for example, natural and synthetic rubbers, silicone rubbers, silicone plastics, polyvinyl chloride (PVC), tetrafluoroethylene polymer, polyethylene, polypropylene, stainless steel, tantalum, nylons, and dacron, have been associated with infections in adjacent body tissues. This phenomenon has been observed especially with indwelling devices; such as, skeletal joint replacements, cardiac valves, indwelling catheters, vascular prostheses, vascular access devices for hemodialysis, cardiac shunts, pacemakers, intrauterine devices, intraperitoneal devices, and organ implants.

The bacteria that cause these infections often grow on the surfaces of these prostheses and are resistant to conventional antibiotic therapy. The bacteria that adhere to the surfaces of the indwelling devices are the same bacteria which, when occurring in the body, can be controlled by conventional antibiotic therapy. However, when these bacteria adhere to the surfaces of an indwelling device they associate in colonies. These colonies are highly resistant to control by conventional antibiotic therapy. The colonies constitute a continual source of bacteria which cause re-infections when conventional antibiotic therapy is withdrawn.

The freely occurring bacteria are planktonic bacteria. The bacteria which cause the recurring infections are sessile bacteria.

Conventional antibiotics are usually effective in controlling the planktonic bacteria in the body, but are not effective in controlling the sessile bacteria.

"indwelling devices" are those biomedical devices which may be implanted in the body of the host so that the biomedical device is in contact with adjacent body tissues.

"Microorganisms" includes living pathogenic bacteria and fungi (including molds and yeasts).

For these reasons, biomedical devices are needed which control the microorganisms which form sessile colonies in living hosts.

This invention provides a biomedical device for controlling bacteria which comprises:
 (a) an elastomer having a Tg below 25° C., selected from natural rubber, synthetic rubber, silicone rubber, polypropylene, polyamide or polyurethane, having incorporated therein or coated thereon,
 (b) an effective amount of an isothiazolone of the formula:

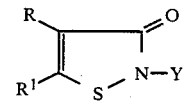

wherein Y is hydrogen, unsubstituted or substituted $C_4$–$C_{18}$ alkyl, unsubstituted or substituted $C_2$–$C_{18}$ alkenyl or alkynyl, an unsubstituted or substituted $C_3$–$C_{12}$ cycloalkyl, unsubstituted or substituted $C_6$–$C_{10}$ aralkyl, or unsubstituted or substituted $C_6$–$C_{10}$ aryl; R is hydrogen, halo, or $C_1$–$C_4$ alkyl; $R^1$ is hydrogen, halo, or $C_1$–$C_4$ alkyl.

If the isothiazolone is unstable, it is stabilized with at least one metal salt in an amount of about 1 to 60 weight percent, based on weight of isothiazolone and metal salt, said metal salt being represented by the formula: $(MX_n)$ wherein M is a cation of a metal selected from sodium, potassium, calcium, magnesium, copper, iron, zinc, barium, manganese, silver, cobalt, or nickel; X is an anion selected from chloride, bromide, iodide, sulfate, nitrate, nitrite, acetate, chlorate, perchlorate, bisulfate, bicarbonate, oxalate, maleate, p-toluenesulfonate, carbonate, or phosphate; and n is an integer for which the anion X satisfies the valence of the cation M.

Preferred isothiazolones are those wherein Y is unsubstituted or substituted $C_6$–$C_{18}$ alkyl, unsubstituted or substituted $C_4$–$C_{18}$ alkenyl or alkynyl, an unsubstituted or substituted $C_5$–$C_{12}$ cycloalkyl, unsubstituted or substituted $C_6$–$C_{10}$ aralkyl, or unsubstituted or substituted $C_6$–$C_{10}$ aryl; R, $R^1$, M, X and n are as defined above. These compounds have a lower water solubility and, therefore, would release slower from the devices than the more water soluble materials.

The most preferred compounds are those isothiazolones wherein Y is $C_6$–$C_{12}$ alkyl, benzyl, phenethyl, halobenzyl, halophenethyl, at least one of R and $R^1$ is chloro or bromo. These compounds have a water solubility of less than 1000 ppm.

This invention also comprises a method for inhibiting the growth of sessile bacteria on a device in a living host which comprises contacting said bacteria with a therapeutically effective amount of microbiocidal material in the biomedical device.

It should be noted that, as the number of carbon atoms in the substituent group "Y" increases, and as halogens are substituted on the isothiazolone ring, water solubility decreases.

"Therapeutically effective amount" is an amount generally in the range of from about 0.03 to about 5 percent by weight and, preferably, in the range of from about 0.05 to 1 percent by weight.

It should be understood that this invention also embraces non-elastomeric materials coated with the products of this invention in a film forming matrix to form devices which perform as well as those prepared solely from elastomers.

"Substituted alkyl" is an alkyl having one or more of its hydrogens replaced by another substituent. Examples include hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, haloalkoxyalkyl, cycloaminoalkyl such as morpholinylalkyl and piperidinylalkyl and pyrrolodinylalkyl and the like, carbamoxyalkyl, alkenyl, haloalkenyl, alkynyl, haloalkynyl, isothiazolonylalkyl, and the like.

"Substituted aralkyl" is an aralkyl having one or more of its hydrogens (either on the aryl or the alkyl) replaced by another substituent. Examples of substituted aralkyls include halo-, lower alkyl-, or lower alkoxy-substituted aralkyl groups.

"Substituted aryl" is an aryl such as phenyl, naphthyl, or pyridyl, having one or more of the hydrogens on the aryl ring replaced by another substituent. Examples of such substituents include halo, nitro, lower alkyl, lower alkoxy, lower alkylamino, acylamino, lower carbalkoxy, sulfonyl, and the like.

The term "isothiazolone(s)" include both the non-complexed 3-isothiazolone(s) and the metal salt complexes of the 3-isothiazolone(s).

Representative "Y" substituents include butyl, hexyl, octyl, decyl, pentadecyl, octadecyl, cyclopentyl, cyclohexyl, benzyl, 3,4-dichloro-benzyl, 4-methoxybenzyl, 4-chlorobenzyl, 3,4-dichlorophenyl, diethylaminoethyl, cyanoethyl, carbomethoxyethyl, 2-methoxy-1-bromoethyl, 3,3,5-trimethylcyclohexyl, phenoxyethyl, 2-chloroanilinomethyl, phenylcarbamoxymethyl, hexenyl, decynyl, carboxyethyl, 1-isothiazolonylethyl, 1,2,2,-trichlorovinyl, phenethyl and p-chlorophenethyl.

Representative "R" substituents include hydrogen, bromo, chloro, iodo, methyl, ethyl, propyl, isopropyl, butyl, and tert-butyl.

Representative "$R^1$" substitutents include hydrogen, chloro, bromo, iodo, methyl, ethyl, propyl, isopropyl, butyl, tert-butyl, chloromethyl, bromomethyl, bromoethyl, and bromopropyl.

Typical compounds within the scope of formula I include: 2-tert-octyl-3-isothiazolone, 2-decyl-3-isothiazolone 2-octyldecyl-3-isothiazolone, 2-cyclohexyl-3-isothiazolone, 4-chloro-2-hexyl-3-isothiazolone, 4-bromo-2-octyl-3-isothiazolone, 5-chloro-2-decyl-3-isothiazolone, 5-chloro-4-cyclohexyl-3-isothiazolone, 4-bromo-5-chloro-2-methyl-3-isothiazolone, 4-bromo-2-cyclohexyl-3-isothiazolone, 4,5-dichloro-2-hexyl-3-isothiazolone, 4-methyl-2-octyl-3-isothiazolone, 4,5-dimethyl-2-octyl-3-isothiazolone, 2-benzyl-3-isothiazolone, 2-benzyl-4,5-dichloro-3-isothiazolone, 2-benzyl-5-chloro-3-isothiazolone, 2-(2',4'-dichlorobenzyl)-3-isothiazolone, 2-(4'-ethylbenzyl)-3-isothiazolone, 2-(3',4'-dichlorophenyl)-3-isothiazolone, 2-(3',3',5'-trimethylcyclohexyl)-3-isothiazolone, 2-(2-phenoxyethyl)-3-isothiazolone, 2-phenylcarbamoxymethyl-3-isothiazolone, 2-(3'-chloro-phenylcarbamoxymethyl)-3-isothiazolone, 2-(3',4'-dichlorophenylcarbamoxymethyl)-3-isothiazolone, 2-[2-(4'-chlorophenyl)ethyl]-3-isothiazolone, 2-n-hexyl-3-isothiazolone, 2-n-heptyl-3-isothiazolone, 2-cyclopentyl-3-isothiazolone, 2-(4'-chlorophenyl)-3-isothiazolone, 2-(2',4'-dichlorophenyl)3-isothiazolone, 2-(2',3'-dichlorophenyl)-3-isothiazolone, 2-(2',5'-dichlorophenyl)-3-isothiazolone, 2-(3'-chlorophenyl)-3-isothiazolone, 2-phenyl-3-isothiazolone, 2-(2'-chlorophenyl)-3-isothiazolone, 2-n-pentyl-3-isothiazolone, 4,5-dichloro-2-tert-octyl-3-isothiazolone, 4-chloro-2-n-octyl-3-isothiazolone, 4-bromo-2-n-octyl-3-isothiazolone, 4-bromo-2-(4'-chlorophenyl)-3-isothiazolone, 4-bromo-2-tert-butyl-3-isothiazolone, 2-trichlorobenzyl-3-isothiazolone, 2-sec-butyl-3-isothiazolone, and 2-(4'-methylphenyl)-3-isothiazolone.

Most preferable are 5-chloro-2-hexyl-3-isothiazolone, 2-n-decyl-3-isothiazolone, 2-n-octyl-3-isothiazolone, 2-cyclohexyl-4,5-dichloro-3-isothiazolone(4,5-dichloro-2-cyclohexyl-4-isothiazolin-3-one), 2-n-butyl-4,5-dichloro-3-isothiazolone, 2-n-octyl-4,5-dichloro-3-isothiazolone (4,5-dichloro-2-n-octyl-4-isothiazolin-3-one), 2-n-octyl-5-chloro-3-isothiazolone and related n-butyl,n-hexyl, n-heptyl and dodecyl compounds; 2-benzyl-4,5-dichloro-3-isothiazolone, 2-(2-phenethyl)-4,5-dichloro-3-isothiazolone, 2-n-dodecyl-3-isothiazolone, 5-chloro-2p-chlorobenzyl-3-isothiazolone (5-chloro-2-p-chlorobenzyl-4-isothiazolin-3-one) and combinations of two or more of said isothiazolones, such as, 5-chloro-2-octyl-3-isothiazolone and 4,5-dichloro-2-octyl-3-isothiazolone.

The preparation and properties of isothiazolones are described in U.S. Pat. Nos. 3,761,488 and 4,105,431. U.S. Pat. No. 3,849,430 discloses a process for preparing isothiazolones. U.S. Pat. Nos. 3,870,795 and 4,067,878 describe metal salt stabilized solutions of 3-isothiazolones.

The 3-isothiazolones used in this invention possess growth inhibiting effects—microbiostatic or microbiocidal or both of them—against a wide variety of microorganisms, including bacteria and fungi, the latter class including molds and yeasts.

The term "control", as employed in the specification and claims means any adverse effect on the existence or growth of any living organism or microorganism which includes a complete killing action (bactericidal action), eradication, or arresting in growth (bacteristatic action).

To further demonstrate the broad-spectrum microbiostatic activity of the 3-isothiazolones against microorganisms known to infect living mammalian hosts the minimum inhibitory concentrations (MIC) of three isothiazolones were determined against a wide variety of organisms, including bacteria and fungi. The results are reported below in Tables I, II and III. Note that these amounts are less than what is contained in the elastomers, but is representative of the minimum amount which must come to the surface of the device to be effective.

TABLE I

Biological Profile of 5-chloro-2-(p-chlorobenzyl)-4-isothiazolin-3-one

|  | MIC, ppm[1] |
|---|---|
| Bacteriostatic Activity | |
| Escherichia coli | 8 |
| Pseudomonas aeruginosa | 8 |
| Staphylococcus aureus | 4 |
| Fungistatic Activity | |
| Candida albicans (yeast) | 4 |
| Aspergillus niger | 4 |
| Aureobasidium pullulans | 8 |

[1]Minimum Inhibitory Concentration, past per million

TABLE II

Biological Profile of 4,5-Dichloro-2-cyclohexyl-4-isothiazolin-3-one

|  | MIC, ppm |
|---|---|
| Bacteriostatic Activity | |
| Escherichia coli | 16 |
| Pseudomonas aeruginosa | 62 |
| Staphylococcus aureus | 10 |
| Fungistatic Activity | |
| Candida albicans (yeast) | 0.5 |
| Aspergillus niger | 0.5 |
| Aureobasidium pullulans | 0.5 |

TABLE III

Biological Profile of 4,5-Dichloro-2-n-octyl-4-isothiazolin-3-one

|  | Active Ingredient MIC, ppm |
|---|---|
| Test Bacterium | |
| Escherichia coli | 16 |
| Pseudomonas aeruginosa | 16 |
| Staphylococcus aureus | 4 |
| Fungistatic Activity | |
| Candida albicans (yeast) | 5 |
| Aspergillus niger | 9 |
| Aureobasidium pullulans | 5 |

Examples 1 to 4 illustrate the fundamental biological activity of the isothiazolones in both polyvinyl chloride and polysilane substrates. Comparisons with commercially available antibiotics in the same substrates are shown in Example 5. Finally, in Examples 6 and 7 actual devices incorporating an isothiazolone are tested for efficacy in resisting infection in animal models.

EXAMPLE 1

Samples of the compounds listed in Table A were added at 0.05, 0.1 and 0.5% by weight in polyvinyl chloride films prepared as follows.

In a two-liter, three-necked, round-bottom, flask equipped with a mechanical stirrer was placed 100 g of polyvinyl chloride, 590 g of reagent grade tetrahydrofuran, and 40.0 g of dioctylphthalate. This was stirred with gentle heating (35°–40° C.) for two hours to completely dissolve the polyvinyl chloride. Then, a barium/calcium salt of a fatty acid (3.5 g), a phosphite chelating agent (1.5 g), stearic Acid (0.25 g) and epoxidized soy bean oil (7.5 g), were mixed with 21 g of tetrahydrofuran and added to the polyvinyl chloride solution. After stirring at room temperature for 30 minutes, the solution was ready for use.

Films containing the isothiazolones were cast by first preparing a 0.5 weight percent polyvinyl chloride solution by adding the isothiazolone to the polyvinyl chloride solution. Then, portions of the 0.5% solution were diluted to 0.1 and 0.05%. The films were drawn down on 12"×12" glass plates using a 50 mil-3" wide coating bar and the films were allowed to air dry for 48 hours.

TABLE A

| No. | Solubility in H$_2$O (ppm) | Name |
|---|---|---|
| 1 | 91 | 4,5-Dichloro-N—cyclohexyl-isothiazolin-3-one |
| 2 | 195 | 4,5-Dichloro-N—benzyl-isothiazolin-3-one |
| 3 | 96 | 4,5-Dichloro-N—2-phenethyl-isothiazolin-3-one |
| 4 | 143 | 4,5-Dichloro-N—n-hexyl-isothiazolin-3-one |
| 5 | 14 | 4,5-Dichloro-N—n-octyl-isothiazolin-3-one |
| 6 | 25 | 4,5-Dichloro-N—n-heptyl-isothiazolin-3-one |

The films were cut into 1.25 cm discs and placed in agar plates inoculated with *Staphlococcus aureus* (S.a) or *Echerichia coli* (E.c.). Zones of inhibition were noted. As noted in Table B, all of the materials showed varying degrees of activity proportional approximately to their aqueous solubility.

The tests demonstrate the effectiveness of the various isothiazolones against both gram positive (S.a.) and gram negative (E.c.) organisms as a function of concentration in poly(vinyl chloride). Compound 1 is the most active under these conditions of test.

TABLE B

| No. | Conc. (%) | Zone of Inhibition (mm) | |
|---|---|---|---|
|  |  | S.a. | E.c. |
| 1 | .05 | 1.8 | 0.8 |
|  | .1 | 4.3 | 1.8 |
|  | .5 | 10.3 | 4.8 |
| 2 | .05 | 2.0 | 0 |
|  | .1 | 3.8 | 0 |
|  | .5 | 10.3 | 3.3 |
| 3 | .05 | 1.8 | 0 |
|  | .1 | 4.3 | 0 |
|  | .5 | 10.8 | 1.8 |
| 4 | .05 | 1.3 | 0 |
|  | .1 | 2.3 | 0 |
|  | .5 | 9.3 | 0.8 |
| 5 | .05 | 0 | 0 |
|  | .1 | 0.3 | 0 |
|  | .5 | 3.3 | 0 |
| 6 | .05 | 0 | 0 |
|  | .1 | 1.3 | 0 |
|  | .5 | 4.3 | 0 |

EXAMPLE 2

In a manner similar to Example 1, compounds 1 and 5 were incorporated at 10, 100 and 1000 ppm in an air curing silicone rubber formulation with methylethyl ketone (60% on silicone rubber) and cast into 15 mil thick films. The films were cut into discs and tested as in example one against S.a. and E.c. The results are shown in Table C.

The results show that both compound 1 and 5 impart bacterial control against both Gram (+) and Gram (−) organisms to slicone rubber when incorporated at levels of 1000 ppm or less. Compound 1 is the more active material.

TABLE C

| No. | Conc. (%) | Zone of Inhibition (mm) S.a. | E.c. |
|---|---|---|---|
| 1 | 10 | 0.8 | 0.1 |
|   | 100 | 6.8 | 5.5 |
|   | 1000 | 16.3 | 13.0 |
| 5 | 10 | 0 | 0 |
|   | 100 | 1.8 | 0 |
|   | 1000 | 8.8 | 0.8 |

EXAMPLE 3

Compound 1 was formulated in vinyl solution as in Example 1 at 1.0 and 5.0% by weight and cast into films. Discs were tested against *Pseudomonas aeruginosa* (P.a.). The 1.0% films gave a slight zone of inhibition while the 5.0% film gave a 1 mm zone of inhibition.

EXAMPLE 4

The films of Example 1 were evaluated against two species of fungi, *Aspergillis niger* (A.n.) and *Aerobasidium pullulans* (A.p). In addition to zones of inhibition, the films were observed by growth of fungus on the film and rated from zero (no growth) to five (heavy growth). The results are summarized in Table D.

The various isothiazolones in polyvinyl chloride film confer marked fungicidal activity against two commercially important species of fungi at levels as low as 500 ppm. They impart zones of inhibition to the surrounding medium as well as prevent growth on the films themselves.

TABLE D

| No. | Conc. (%) | Zone of Inhibition (mm) A.n. | A.p. | Growth on Film A.n. | A.p. |
|---|---|---|---|---|---|
| 1 | 0.05 | 0 | 0 | 1 | 0 |
|   | 0.1 | 0 | 0 | 0 | 0 |
|   | 0.5 | 5.3 | 5.3 | 0 | 0 |
| 2 | 0.05 | 0 | 0 | 4 | 4 |
|   | 0.1 | 0 | 0 | 0 | 0 |
|   | 0.5 | 4.3 | 4.8 | 0 | 0 |
| 3 | 0.05 | 0 | 0 | 1 | 2 |
|   | 0.1 | 0 | 0 | 0 | 0 |
|   | 0.5 | 4.8 | 3.8 | 0 | 0 |
| 4 | 0.05 | 0 | 0 | 0 | 3 |
|   | 0.1 | 0 | 0 | 0 | 0 |
|   | 0.5 | 3.8 | 2.8 | 0 | 0 |
| 5 | 0.05 | 0 | 0 | 5 | 5 |
|   | 0.1 | 0 | 0 | 3 | 3 |
|   | 0.5 | 0 | 0 | 0 | 1 |
| 6 | 0.05 | 0 | 3 | 0 | 3 |
|   | 0.1 | 0 | 1 | 0 | 2 |
|   | 0.5 | 0 | 0 | 0 | 0 |

EXAMPLE 5

A series of commercial antibiotics were evaluated in polyvinyl chloride films (as in Example 1) and silicone films (as in Example 2). The antibiotics were thoroughly blended with the appropriate polymers in solution at 0.05, 0.2, 1.0 and 5.0 percent levels of antibiotic by weight until uniform, and the resulting mixtures were cast into films and tested for zone of inhibition, as in Example 1. The results are shown in Table E.

These results demonstrate the essential equivalency of Compound 1 as a bacteriocide to the best commercial antibiotics. In addition, as the plates were allowed to incubate, it was noted that those with antibiotics were soon overgrown by fungi, whereas the plates with Compound 1 were clean. Most importantly was the presence of resistant bacterial colonies that appeared in the antibiotic plates with time as the resistant species began to grow. Thus, Compound 1 demonstrates broad spectrum, bacterial and fungal, control and the ability to suppress all species and not permit the growth of antibiotic resistant species.

TABLE E

| Compounds | Conc. (%) | (Zones in mm) PVC E.c. | S.a. | P.a. | Silicone E.c. | S.a. | P.a. |
|---|---|---|---|---|---|---|---|
| T[1] | .04 | 0 | 0 | 0 | 0 | 6.3 | 10.3 |
|   | .20 | 5.8 | 0 | 0 | 5.8 | 15.8 | 0.3 |
|   | 1.0 | 0 | 11.3 | 0 | 9.8 | 21.3 | 0 |
|   | 5.0 | 12.8 | 19.8 | 0 | 19.8 | 26.3 | 0 |
| P[2] | .04 | 0 | 0 | 0 | 0 | 0 | 0 |
|   | .20 | 0 | 0 | 0 | 0.8 | 0 | 0 |
|   | 1.0 | 0 | slight | 0 | 13.3 | 14.8 | 5.3 |
|   | 5.0 | 12.3 | 13.8 | 9.8 | 17.3 | 21.3 | 13.3 |
| G[3] | .04 | 0 | slight | 0 | 4.8 | 5.8 | 0 |
|   | .20 | 5.8 | 5.3 | 3.3 | 7.8 | 7.3 | 5.3 |
|   | 1.0 | 5.8 | 5.8 | 5.3 | 10.3 | 8.8 | 5.8 |
|   | 5.0 | 9.3 | 7.8 | 6.8 | 12.3 | 12.8 | 9.8 |
| Compound 1 | .20 | — | — | — | 14.3 | 17.8 | 0.8 |
|   | 1.0 | — | — | — | 16.3 | 20.3 | 3.3 |
|   | 5.0 | — | — | — | 16.3 | 20.3 | 3.3 |
| Control |   | 0 | 0 | 0 | 0 | 0 | 0 |

T[1] = Tetracycline - HCl
P[2] = Piperacillin - Na
G[3] = Gentamycin sulfate

EXAMPLE 6

A silicone rubber used for the manufacture of urinary catheters is blended on a mill with 0.05, 0.1, 0.5, 1.0 percent levels by weight of Compound 1 until uniform and formed into catheters by the usual procedure. These are inserted into large male dogs held in restraining harnesses. The catheters are examined for visible growth and cultured onto agar over a period of one week. The results are shown in Table F.

The results demonstrate the efficacy of the biocide Compound 1 treated silicone catheter in resisting sessile colonization by bacteria or fungi.

TABLE F

| Culture | | Implanted Catheters One Week Visual Examination | Agar |
|---|---|---|---|
| Control | | slimy | +4 |
| Compound 1 | .05 | slight slime | +2 |
|   | 0.1 | clean | +1 |
|   | 0.5 | clean | 0 |
|   | 1.0 | clean | 0 |

EXAMPLE 7

Pacemakers are dipped into solutions of polyvinyl chloride containing various levels of Compound 1 (0.05-1.0%) and the resultant device dried to form a tight surface film of polyvinyl chloride. The devices are inserted into dogs and allowed to remain without electrical activation for a period of one month. The devices are then removed and examined visually and by agar cultures from the surface. The results are summarized in Table G.

The results demonstrate the efficacy of Compound 1 treated polyvinyl chloride in resisting sessile colonization, particularly as compared to untreated control.

TABLE G

| | Implanted Pacemakers | |
|---|---|---|
| Culture | One Month Visual Observation | Agar |
| Control | slime covered | +4 |
| Compound 1 .05 | slime covered | +3 |
| 0.1 | slight slime layer | +1 |
| 0.5 | clean | trace |
| 1.0 | clean | 0 |

What is claimed is:

1. A biomedical device selected from a skeletal joint replacement, cardiac valve, indwelling catheter, vascular prostheses, vascular access device, cardiac pacemaker, intrauterine device, intraperitoneal device or organ implant prepared from an elastomer having a Tg below 25° C. selected from natural rubber, synthetic rubber, silicone rubber, polypropylene, polyamide or polyurethane having incorporated therein or coated thereon from 0.03 to about 5 percent of an isothiazolone of the formula:

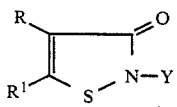

wherein Y is hydrogen, unsubstituted $C_4$-$C_{18}$ alkyl, hydroxyalkyl, haloalkyl, cyanoalkyl, alkylaminoalkyl, dialkylaminoalkyl, arylaminoalkyl, carboxyalkyl, carbalkoxyalkyl, alkoxyalkyl, aryloxyalkyl, alkylthioalkyl, arylthioalkyl, haloalkoxyalkyl, cycloaminoalkyl, or carbaloxyalkyl, unsubstituted $C_4$-$C_{18}$ alkenyl, haloalkenyl or unsubstituted alkynyl, haloalkynyl and unsubstituted $C_3$-$C_{12}$ cycloalkyl, 3,3,5-trimethylcyclohexyl, unsubstituted aralkyl of 6-10 carbon atoms, haloaralkyl, lower alkyl aralkyl, lower alkoxyaralkyl, or unsubstituted aryl of 6-10 carbon atoms, or phenyl, naphthyl, or pyridyl substituted with one or more halo, nitro, lower alkyl, lower alkoxy, lower alkylamino, acylamino, lower carbalkoxy, or sulfonyl; R is hydrogen, halo, or $C_1$-$C_4$ alkyl; and $R^1$ is hydrogen, halo, or $C_1$-$C_4$ alkyl.

2. The device of claim 1 wherein the isothiazolone is stabilized with at least one metal salt used in an amount of about 1 to 60 weight percent, based on weight of isothiazolone and metal salt, said metal salt being represented by the formula: $(MX_n)$ wherein M is a cation of a metal selected from sodium, potassium, calcium, magnesium, copper, iron, zinc, barium, manganese, silver, cobalt, or nickel;

X is an anion selected from chloride, bromide, iodide, sulfate, nitrate, nitrite, acetate, chlorate, perchlorate, bisulfate, bicarbonate, oxalate, maleate, p-toluenesulfonate, p-toluene, carbonate, or p-toluenephosphate; and n is an integer for which the anion X satisfies the valence of the cation M.

3. The device of claim 1 which contains from about 0.05 to about 1.0 percent by weight of isothiazolone.

4. The device of claim 1 wherein isothiazolone has the following substituents, Y is unsubstituted or substituted $C_6$-$C_{18}$ alkyl, unsubstituted or substituted $C_3$-$C_{12}$ cycloalkyl, or unsubstituted or substituted $C_6$-$C_{10}$ aralkyl, and R and $R^1$ are the same or different radical selected from hydrogen, halo, or $C_1$-$C_4$ alkyl.

5. The device of claim 4 wherein the isothiazolone has the following substituents; Y is $C_6$-$C_{18}$ alkyl, or unsubstituted $C_3$-$C_{12}$ cycloalkyl, and R and $R^1$ are the same or different radical selected from hydrogen or chloro.

6. The device of claim 5 wherein the isothiazolone is selected from 4,5-dichloro-N-cyclohexyl-isothiazolin-3-one; 4,5-dichloro-N-benzyl-isothiazolin-3-one; 4,5-dichloro-N-2-phenethyl-isothiazolin-3-one; 4,5-dichloro-N-n-hexyl-isothiazolin-3-one; 4,5-dichloro-N-n-octyl-isothiazolin-3-one; 4,5-dichloro-N-n-heptyl-isothiazolin-3-one; 5-chloro-N-(p-chlorobenzyl)isothiazolin-3-one; or combinations thereof.

7. The device of claim 6 wherein the isothiazolone is a combination of 4,5-dichloro-N-cyclohexyl-isothiazolin-3-one and 4,5-dichloro-N-n-octyl-isothiazolin-3-one.

8. The device of claim 1 which is selected from skeletal joint replacements, cardiac valves, indwelling catheters, vascular prostheses, vascular access devices, cardiac pacemakers, intra-uterine devices, intraperitoneal devices, or organ implants made from synthetic materials.

9. A method for controlling bacteria which form a colony resistant to conventional antibiotic therapy which comprises employing the device of claim 1 as an indwelling device.

10. A method for controlling bacteria which form a colony resistant to conventional antibiotic therapy which comprises employing the device of claim 2 as an indwelling device.

11. A method for controlling bacteria which form a colony resistant to conventional antibiotic therapy which comprises employing the device of claim 3 as an indwelling device.

12. A method for controlling bacteria which form a colony resistant to conventional antibiotic therapy which comprises employing the device of claim 4 as an indwelling device.

13. A method for controlling bacteria which form a colony resistant to conventional antibiotic therapy which comprises employing the device of claim 5 as an indwelling device.

14. A method for controlling bacteria which form a colony resistant to conventional antibiotic therapy which comprises employing the device of claim 6 as an indwelling device.

15. A method for controlling bacteria which form a colony resistant to conventional antibiotic therapy which comprises employing the device of claim 7 as an indwelling device.

16. A method for controlling bacteria which form a colony resistant to conventional antibiotic therapy which comprises employing the device of claim 8 as an indwelling device.

* * * * *